(12) United States Patent
McLeod

(10) Patent No.: US 7,354,156 B1
(45) Date of Patent: Apr. 8, 2008

(54) NATUROPTIC METHOD FOR RESTORING HEALTHY VISION

(76) Inventor: Roger D McLeod, 636 Varnum Ave., Lowell, MA (US) 01854

( * ) Notice: Subject to any disclaimer, the term of this patent is extended or adjusted under 35 U.S.C. 154(b) by 33 days.

(21) Appl. No.: 11/465,202

(22) Filed: Aug. 17, 2006

(51) Int. Cl.
*A61B 3/02* (2006.01)

(52) U.S. Cl. ................................. 351/239; 351/203

(58) Field of Classification Search .............. 351/200, 351/202, 203, 239–243
See application file for complete search history.

(56) References Cited

U.S. PATENT DOCUMENTS

| | | | |
|---|---|---|---|
| 4,660,948 A * | 4/1987 | Retz | 351/239 |
| 5,309,185 A | 5/1994 | Harper | |
| 5,812,239 A | 9/1998 | Eger | |
| 6,379,007 B1 * | 4/2002 | Farb | 351/239 |
| 6,851,807 B2 | 2/2005 | Holdeman | |

* cited by examiner

Primary Examiner—Huy K Mai
(74) Attorney, Agent, or Firm—Mark P. White (57) ABSTRACT

A method for restoring healthy vision includes first establishing a visual target, then having the subject keep horizontal and vertical lines, through the center of the plane of the target, respectively parallel to corresponding horizontal and vertical lines through the centers of the eyes, and fixing the eyes on the central part of the target while performing all the following steps, taken in order, which include slowly rotating the head to the right about five degrees, keeping the eyes horizontally aligned, then stopping and performing about four eye blinks, then repeating the rotation and blinks in five-degree increments until an excursion of about 30 degrees is reached, then repeating the procedure to the left, until and excursion of about 30 degrees to the left of center is reached, then repeating the procedure again to the right, until the nose is pointing directly at the target.

11 Claims, 6 Drawing Sheets

Vertical line through target on chart and vertical lines through pupils of eyes must stay parallel during right and left head rotations

Horizontal lines through target on chart and horizontal lines through pupils of eyes must stay parallel during up and down head rotations

Fig. 6

NATUROPTIC METHOD FOR RESTORING HEALTHY VISION

DISCUSSION OF THE PRIOR ART

In the following discussion, reference is made to the physiology of the human eye. The discussion can be best understood by referring to FIGS. 1, 2 and 3, which depict the human eyeball in its various aspects.

In a healthy eye, light reflecting from a sighted object produces an extremely large set of diffraction patterns, spread across the visible spectrum. At any instant, only two diffraction patterns are useful; the shorter wavelength interval interacts with cone ends and the slightly longer one interacts with rod ends. These diffraction patterns convey object information, and typically will be about twenty nanometers apart.

Figure 1:
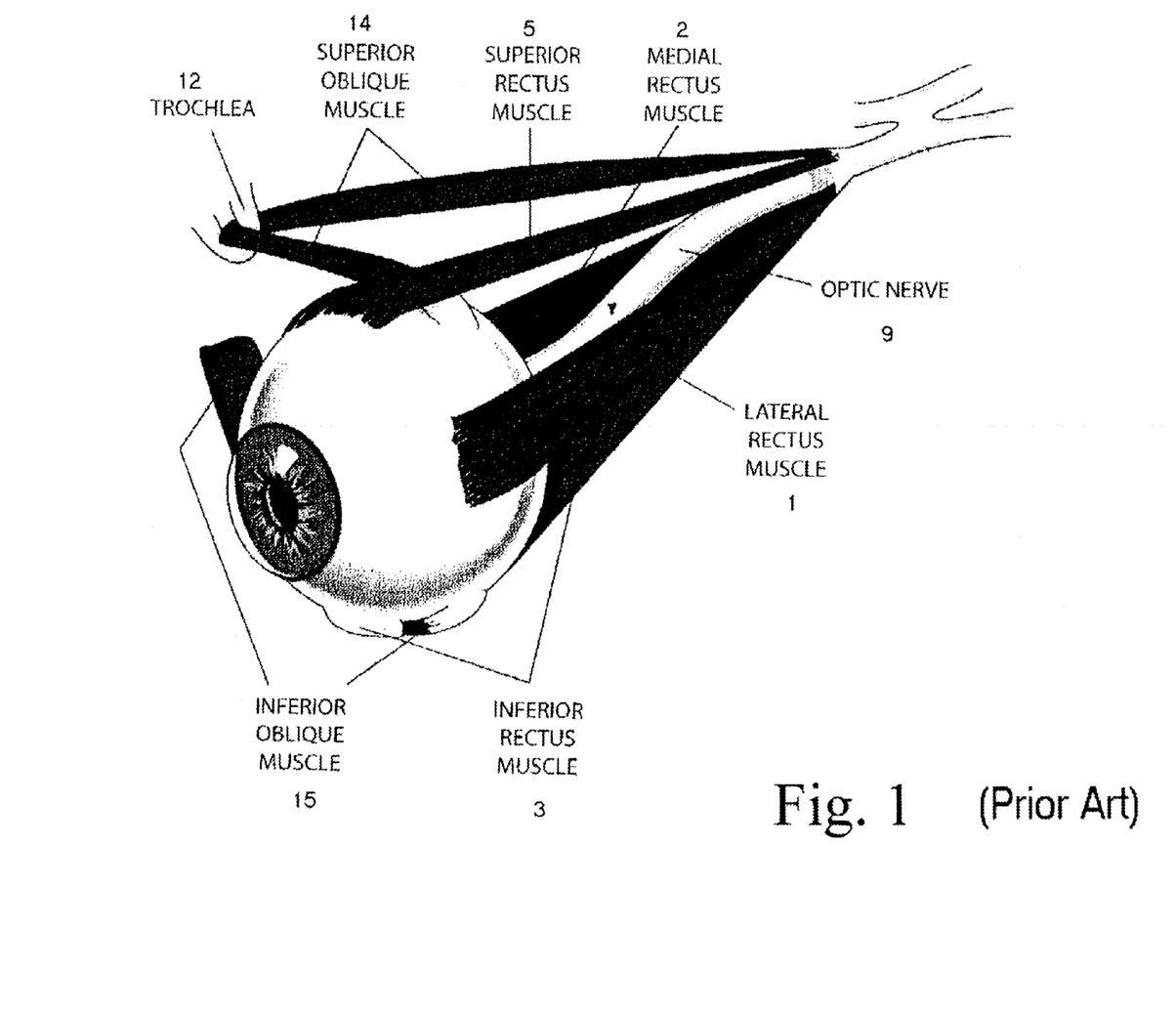
FIG. 1 depicts a perspective view of the left eyeball, showing the extrinsic muscles

An unhealthy eye is defined herein as an eyeball deformed by self-induced vision abuse. Incorrect and effectively static stresses in the large external (extrinsic) eye muscles, as shown in FIG. 1, cause the two diffraction patterns to be displaced and replaced with parts of many separate diffraction patterns. These muscles may be seen, still referring to FIG. 1, in which the extrinsic muscles are shown as reference numbers 1, 2, 3 and 5.

Restoration to a healthy eye can be accomplished by rebalancing the muscle state. Correct information transfer and proper vision can return because that balanced muscle state can provide precisely two diffraction patterns, one in coincidence with foveal 13 cone ends and rods, and the other diffraction pattern is coincident with parafoveal cone ends. This requires adjusting the proper external muscles with appropriate procedures that restore ordinary muscle flexibility. In addition, those muscle strengths must be controllable so that they can reshape the eye to place a correct pair of wavelengths into coincidence with cone and rod ends.

Muscle flexibility can be achieved with safe techniques that mimic ordinary eye and head movements. Making the returned flexibility useful is accomplished by means of simple and specific blinking of the unhealthy eye. This can be done under conditions that replicate the extremes of illumination normally encountered by a healthy eye.

Figure 2:
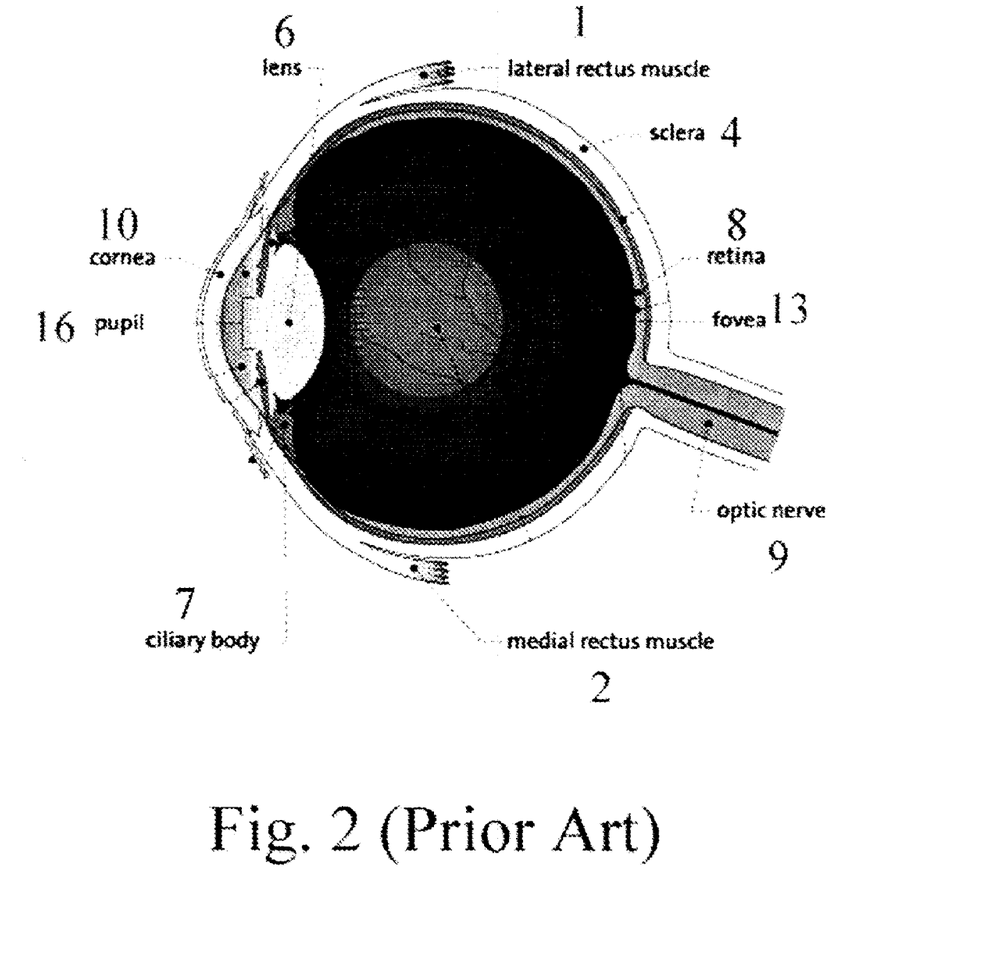
FIG. 2 depicts a side elevation cross-section view of the eyeball, showing elements thereof.

The important and nearly instantaneous aspect of blinking for vision is to cause minor shape changes in the lens. Referring now to FIG. 2, Lens 6 shape is controlled by the ciliary muscles 7 that surround its periphery. Nerve 9 loops interconnected to the retina 8 and ciliary muscles 7 provide signals to appropriate extrinsic eye muscles. These loops are also known as feedback loops. These signals cause the extrinsic muscles to reshape the eye, which in turn will restore a correct diffraction pattern pair at the retina 8.

Pupil 16 diameter (aperture diameter, a) increases or decreases with changes in light intensity. Diameter changes force small changes in the focal length of the crystalline lens. These lens changes combine with the light converging power of the rest of the eye to give a total eye focal length f. An eye's visible spectrum covers the range from violet to red light, and is described by wavelength (lambda, $\lambda f2$), that can change by a factor of about two.

Figure 3:
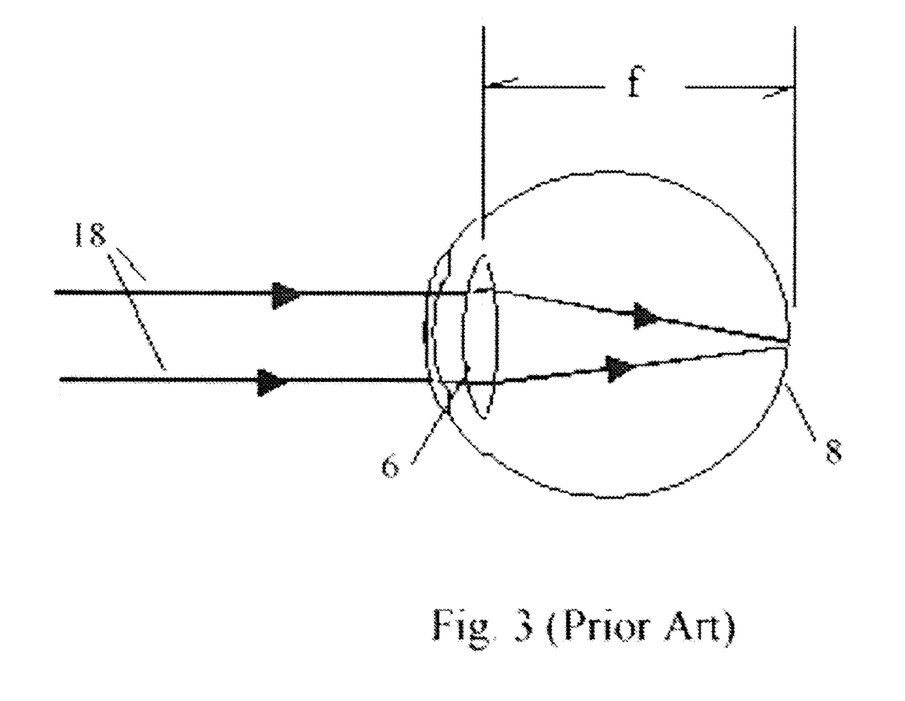
FIG. 3 depicts a side elevation cross-section view of the eyeball, showing the focusing of incident rays on the retina.

Referring now to FIG. 3, a healthy eye is shown, wherein incident light rays 11 are seen entering the eye and being focused by the lens 6 so that they meet at the retina 8. The lens 6 has a focal length f, that which is necessary so that the light rays focus exactly on the retina, rather than in front or in back.

The above factors are included in the following equation that describes the radius r to the first zero of the diffraction pattern of a circular aperture. The expression cited is also known as the Airy disk radius formula. Its origin, and the implications for healthy vision from this equation are presented later.

That radius is:

$$r = 1.22 \lambda f2 f/a$$

wherein $\lambda$ is the wavelength of the light being diffracted;

f2 is the focal length to the retina;

f is the actual focal length of the eye; and a is the aperture diameter.

The formula, as defined in detail, shows why pupil 16 diameter changes are relevant, and require reengaging more flexible extrinsic eye muscles. When the diameter a of the aperture (the pupil 16 size) changes, the formula shows that the product of wavelength and eye focal length must change.

The extrinsic muscles are required to force the product value of the wavelength and whole-eye focal length to vary appropriately following those feedback instructions received from the nerve 9 loops of the retina and the ciliary muscles 7 that interconnect to the extrinsic muscles.

Eye shape and net eye focal length change because of the nerve 9 loops that feed signals back systematically to the larger external eye muscles. These force compensating changes to be made in the overall eye shape.

The minor lens changes mentioned have a direct consequence. They move diffraction patterns, by a small amount, further away from the lens, and then cause them to move collectively slightly closer to the lens. This describes the searching aspect initiated by blinking and the crystalline lens that allows sensors to detect either an improvement of vision or increased blurring of vision. That searching causes corrective feedback signals to be sent from nerves associated with the ciliary 7 fibers and the detection process to the major external muscles, called extrinsics, attached to each eye. If those extrinsic muscles remain flexible and are receiving appropriate adjustment signals, they are capable of effecting the major changes required according to the formula for the particular radius associated with each separate pupil 16 diameter.

A naturally functioning human pupil 16 can readily be observed changing its effective aperture diameter in the way cited, whenever light levels change, or following normal blinking. Observers can detect those changes, and each blink actually causes slight, three-dimensional shifts in the shape of the crystalline lens. These lens changes can be detected visually when a distant light is reflected from its front, or anterior, surface. The posterior surface also changes, but to a lesser degree because it is relatively flatter.

Therefore, the effect of blinking is to induce crystalline lens changes in optical power of up to plus or minus three tenths of a diopter, relative to the lens baseline, or non-blinking, state. Those values are superimposed onto the total net converging power of an average eye, which can be taken as about sixty diopters. The truly remarkable thing is that the overall size of the oscillation just described here is only six-tenths of a diopter, one-hundredth of the optical power of an eye, yet the blinking must be fulfilling some important role.

These pupil-related observations show that the crystalline lens 6 is involved in feedback loops involving the major eye-shaping extrinsic muscles, so that the lens cannot be playing the major direct accommodative role assigned to it by prior art vision modelers. The present invention is based on the recognition that these extrinsic muscles must maintain their flexibility in order for the eye to function properly.

Many of the major functional vision shortfalls can be caused by inflexibilities in one or more of these six extrinsic eye muscles. Of those extrinsics, four are in the recti group consisting of a lateral rectus 1 on the outer side of either eye, and on the inner, nasal side, the medial rectus; the superior rectus 5 is attached at the top of each eye, while the Inferior rectus muscle 3 is attached to the lower part of the sclera 4, just below each eye.

The four of these extrinsics for each eye are attached to the white, scleral 4 part of the eye just out of sight within the area blocked by the front of the eye socket, and its soft-tissue surround. These four have their other ends jointly attached to the eye socket, behind the eye. A left eye has its lateral muscle on its left side, so the medial rectus for it is at its right. Generally, uniform, simultaneous contraction of all of these four extrinsic muscles shortens the eye length that corresponds to a shorter focal length. The Airy disk radius formula as described above indicates that this requires that two shorter wavelength intervals will simultaneously and continuously move into coincidence with rod and cone ends as increasing light levels drive decreasing pupil 16 size.

The two remaining extrinsic muscles consist of the superior and inferior oblique muscle pair, that shares their rear attachment point with the four extrinsic recti muscles. The front attachments of the obliques are reached through trocleal openings, for the right eye, that redirect their directions, which generally are comparable in direction to that of the recti. Once through the trochlea 12, as seen in FIG. 1, each one has an approximately perpendicular orientation to its original course. These ends then attach to the sclera 4 near, and also approximately perpendicular to, the superior 5 and inferior 3 recti. If the four recti muscles 1,2,3 and 5 remain sufficiently flexible or labile, then decreasing light levels will, according to eye physiology as described above, be accompanied by larger pupil 16 diameters, requiring longer wavelengths and focal lengths. These will be provided upon uniform, simultaneous contraction of the two oblique muscles that can lengthen the eyes.

Because of the attachment points of the superior 14 and inferior 15 oblique muscle pair, the obliques 14, 15, working separately, can rotate the eyeball clockwise or counterclockwise relative to a front-on view. I have detailed below, in the discussion related to strabismus, some serious visual consequences that can be generated in responses to inappropriate locked-in tensions in these obliques 14, 15, always elicited in response to excessive muscle tension elsewhere in the extrinsics 1,2,3 and 5. Those same obliques, working in tandem and simultaneously in contraction do provide proper eyeball lengthening, absent static recti.

These six muscles and their tensions, in unbalanced or excess amounts, relate in part to the development of defect of aiming appropriately at targets for near vision and for far vision.

An unhealthy eye can be nearly "frozen" into inappropriately adjusted, nearly statically locked states when the extrinsic muscles lose their flexibility and tone. However, with processes described and practiced in accordance with the present invention, it is possible to correct those states.

These processes can quickly restore greatly improved vision for 'nearsighted', 'farsighted' and presbyopic individuals. These states are a result of statically fixed external eye muscles. These vision defects are reversible. The procedures described herein reestablish appropriate flexibility ranges for the six extrinsic eye muscles. These, in defective vision, have become essentially locked in place, creating a type of static muscular state, which for an eye is analogous to any vehicle stuck in a rut.

The approach of the present invention includes the only model that is theoretically well grounded, effective, and powerful, and is different from other vision correction procedures. This approach demonstrates why feedback, from small oscillations of the crystalline lens 6 activated by blinking, drives the correction process, and is supported by known empirical facts. It also works more quickly than any other competing healing protocol.

The steps described in this invention release the eye's optics from its rigid self-created lock, while they improve or repair vision. They can simultaneously teach what to do to avoid damaging vision again, as part of their processes. Furthermore, they can be used to maintain improvements even in the face of job and/or academic pressures. These, if left unresolved, could reestablish the original defective visual state, or even make the original state worse.

SUMMARY OF THE INVENTION

It is an objective of the present invention to provide a method to correct vision defects without the use of corrective lenses and without the use of surgery.

In accordance with a first aspect of the invention a method for restoring healthy vision to the damaged eyes of a subject includes the steps of first establishing a visual target.

In accordance with a second aspect of the invention, during the entire time of the method the subject keeps a vertical line through said visual target parallel to corresponding vertical lines through the centers of the planes of the pupils 16 of the eyes for horizontal angular head displacements.

In accordance with a third aspect of the invention the subject maintaining a line horizontally through the pupils' centers parallel to a horizontal line through the visual target during vertical angular displacements of the head.

In accordance with a fourth aspect of the invention the subject maintains the fixation of the eyes on the central part of the visual target while rotating the head to a first angle, blinking the eyes several times, and rotating the subject's head in the reverse direction.

In accordance with a fifth aspect of the invention, the rotation of the head is done by the method which includes (a) starting from a value of j=0, and where the starting horizontal and vertical angular displacements of the head are (0,0), and while incrementing the index i by 1, slowly rotating the subject's head by a first angle approximately $\alpha(j)\beta(j)$, where $\alpha$ is the ith horizontal excursion and $\beta(j)$ is the jth vertical excursion.

In accordance with a sixth aspect of the invention the subject next stops said rotating and performs about n eye blinks.

In accordance with a seventh aspect of the invention the subject repeats the previous steps until the total of $\tau$ steps are taken.

In accordance with an eighth aspect of the invention the vertical displacements $\beta(j)$ are equal to zero for all values of j, so that the head rotates only in the horizontal direction.

In accordance with a ninth aspect of the invention, after j1 steps the head is at a maximum excursion $\tau 1$ to one side, after j2 steps more, the head is at a maximum excursion $-\tau 1$ to the other side, and after j3 steps more, the head returns to a position of (0,0).

In accordance with a tenth aspect of the invention the horizontal displacements α(j) are equal to zero for all values of j, so that the head rotates only in the vertical direction.

In accordance with an eleventh aspect of the invention, after j1 steps the head is at a maximum vertical excursion τ2, after j2 steps more, the head is at a minimum excursion −τ2; and after j3 steps more, the head returns to a position of (0,0).

In accordance with a twelfth aspect of the invention the vertical displacements β(j) are equal to zero for the first k values of j, so that the head rotates only in the horizontal direction for these values, the horizontal displacements α(j) are equal to zero for the next l values of j, so that the head rotates only in the vertical direction for these values, and the vertical displacements β(j) are equal to zero for the next 2k values of j, so that the head rotates only in the horizontal direction for these values, and in the direction opposite that of the first step above, and having a total excursion equal to twice the magnitude and opposite in direction to the first step above.

In accordance with a thirteenth aspect of the invention the horizontal displacements α(j) are equal to zero for the next l values of (j) so that the head rotates only in the vertical direction for these values, and in the opposite direction of the second step above and having a total excursion equal in magnitude and opposite in direction to the second step above, so that the subject's head describes a "box" pattern, returning to the point of origin at the conclusion of the steps.

In accordance with a fourteenth aspect of the invention the number of eye blinks is approximately four.

In accordance with a fifteenth aspect of the invention the visual target comprises a field of high-contrast combination of thin letter, number, or symbol sequences on a rigid background.

In accordance with a sixteenth aspect of the invention the visual target is created by the steps of placing a substantially opaque cover over both eyes, positioned so that the eyes can blink freely and fully while ensuring that no light at all can be detected by the eyes and sounding a distant, centrally located audible signal as an aiming cue, or its equivalent.

In accordance with a seventeenth aspect of the invention, the distant, centrally located audible signal is generated at the location of the visual target.

In accordance with an eighteenth aspect of the invention each horizontal rotation of the subject's head α(j) has an approximate magnitude of 5 degrees for all values of j.

In accordance with a nineteenth aspect of the invention each horizontal rotation of the subject's head α(j) has an approximate magnitude of 5 degrees for all values of j.

In accordance with a twentieth aspect of the invention each vertical rotation of the subject's head β(j) has an approximate magnitude of 2 degrees for all values of j.

In accordance with a twenty-first aspect of the invention each vertical rotation of the subject's head β(j) has an approximate magnitude of 2 degrees for all values of j.

BRIEF DESCRIPTION OF THE DRAWINGS

These, and further features of the invention, may be better understood with reference to the accompanying specification and drawings depicting the preferred embodiment, in which.

FIRST PREFERRED EMBODIMENT

The term "Naturoptics" describes the method described herein. The term was first used by the inventor, Prof. McLeod, in a Joint meeting of the New England and section of the American Physical Society and the American Association of Physics Teachers. The term "Naturoptics" is used to mean techniques for healing, improving or correcting vision naturally, without total reliance on the use of glasses, contact lenses, or surgery.

The method of this invention has been empirically established, and has demonstrated that 'damaged' eyes, without glasses or other corrective contacts, can be restored to healthy vision.

In the following description the term "approximate" is used in describing angles. This terms shall be construed to mean plus or minus ten percent hereinafter.

When the term "approximate" is used in describing the number of eye blinks, it shall be construed to mean within ten percent less, or twenty-five percent more, rounded up to the nearest integer value.

The first step is to establish a visual target, which is established by setting any high-contrast combination of thin letters, numbers or symbol sequences on a rigid background at an appropriate distance. For right to left, or vice versa, head rotations, vertical lines, (to be considered to be), through the centers of the planes of the pupils 16, must stay parallel to a similar vertical line through the central viewed area of this visual target, which is to be mounted on a vertical surface or its equivalent. Corresponding horizontal lines on the target and through the eye pupils 16 must remain parallel during "up or down head rotations." (Ref figures)

The visual target can be programmed to be generated on any type of computer, monitor display or their equivalent, including playing onto a television, movie or projection screen. For optimum efficiency in effecting visual repair, these devices should be situated such that lines corresponding to those as described above remain respectively parallel.

Initially, the visual target is to be positioned at that distance which provides clearest uncorrected vision.

To improve near vision, the observation distance is shortened so that the target object in the field of view is just noticeably blurred beyond the visual acuity established above.

Severely myopic individuals, (extremely blurred distant vision), may require starting at some distance close enough to the target such that at least one symbol is recognizable, with the best vision achievable, and then working outwards away from the target, as improvement is achieved.

If the task is to improve distance vision, then the distance at which clearest perception of an object is achieved is slightly increased until the visual target is just noticeably blurred.

Figure 4:
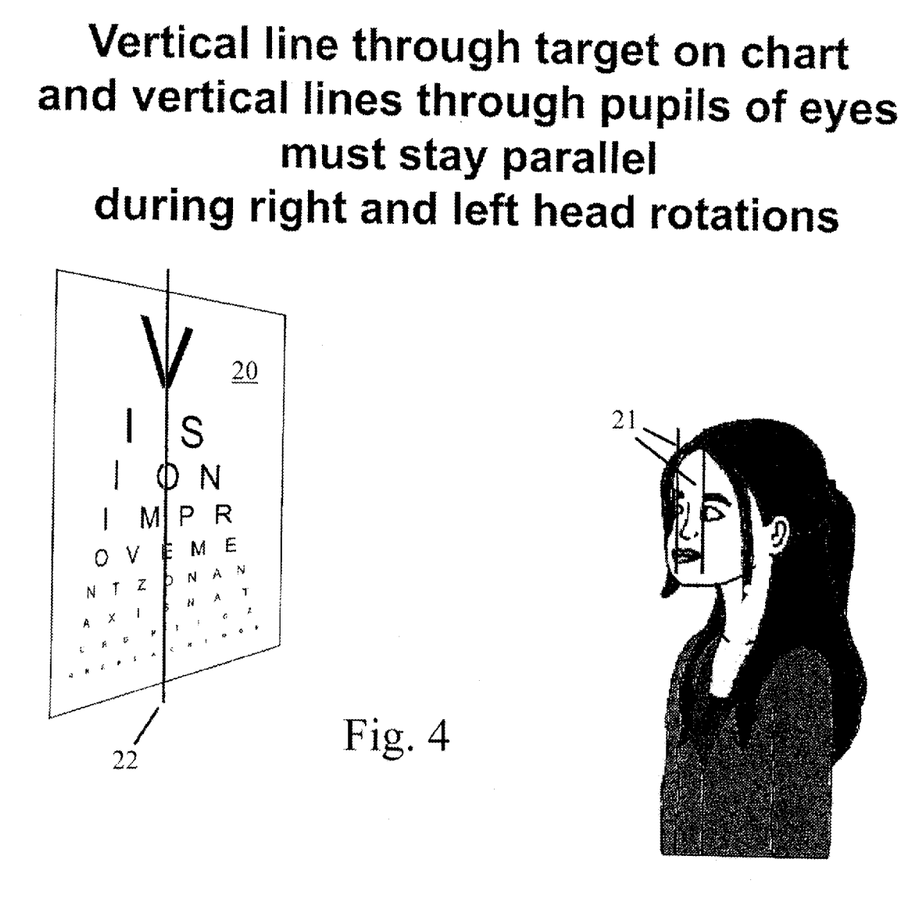
FIG. 4 depicts a subject focusing on a target chart while maintaining vertical stability during horizontal head rotation.

Then, the procedure to restore muscle lability must include the following steps, as depicted in FIG. 4: while maintaining the fixation of the eyes on the central part of the now just-slightly-blurred target 20, begin by slowly rotating the head to the right about five degrees, keeping the eyes horizontally aligned; then stop and do about four eye blinks. Repeat this procedure, in five-degree increments, only up to that angular location at which the nose just begins to block part of the field of view of the right eye. The total angular displacement backward from where the nose finally points, relative to where it started, should be about thirty degrees. This can be located and tested by covering the left eye's view, or some equivalent strategy.

During this procedure it is essential that the subjects head does not tilt or twist. This is effected by maintaining imaginary vertical lines 21 through the subjects eyeballs parallel with an imaginary vertical line 22 through the target.

The angular size of the full moon, or of the sun, is about one-half of one degree, so that the angular fixation points at which each stop must be: made, with four or so accompanying blinks, should approximate the side-by-side width of ten full moons, (or suns).

Once the maximum rightward angular visual displacement, with uncovered eyes, has been achieved, then leftward excursion is established, also in approximately five-degree steps. Continue blinking, as defined, at each stop-point. Work along this leftward direction until the point is reached at which the nose just begins to block the field of view for the left eye. Reverse directions, continuing the cycle until the nose is at the center, and the eyes again both symmetrically aim at a central region. One complete additional horizontal cycle, at least, should be repeated.

Initially, some individuals may find it more convenient to work gradually toward reaching maximum rightward or leftward angular displacements. Maintaining visual comfort can be used to establish appropriate vision improvement rates.

This new procedure, as the head rotates toward an extreme rightward pointing position chosen for the nose, with the right (and left) eye(s) aimed leftward toward the target's central region, gradually induces the left eye's medial rectus muscle to be extended out of any previously semi-fixed, and likely over-contracted state. That same left eye's outer, lateral rectus muscle simultaneously is required to increase its contraction capability, while the lateral rectus is forcing the medial rectus to extend gradually and appropriately.

This action, always to be reached in stages appropriate for that individual's eye muscle condition, leads to increasing the range of flexibility of those muscles. Excursions to the farthest leftward sense, as each individual can gradually reach them, are especially effective in stretching the right eye's medial rectus muscle, as it is drawn out of its semi-rigid self-imposed 'prison' of inflexibility that had at least partially immobilized visual adjustability of the eyeball, in gradual stages, that created some original visual problems. The regained flexibility was induced by the contraction that was gradually achieved in this process by the tightening up, of the right eye's lateral rectus muscle, out of its own previously semi-rigid 'rut' of over-extension.

The complete safety of this angular displacement procedure can be recognized by comparison with what is done during the activities of shaving, or putting on makeup for women, on the far left (or alternately, far right) side of the face, while looking in the mirror. Those activities require the same rightward (or leftward) pointing of the nose while both eyes are simultaneously visually fixating in the opposite angular sense of the nose displacement, on the shaving, or make-up application point.

The exceedingly important visual effects of blinking, emphasizing its involvement in feedback signals.

Feedback is mediated by way of nerve 9 loops, from the retinal detectors and the ciliary muscle 7 pathways, to the powerful extrinsic muscles. These then adjust, appropriately and individually, from prior tension states. This is to correct diffraction pattern readings at the retina that are just noticeably blurred, by adjusting muscular tensions, as long as they have retained or recovered their dynamic adjustment capabilities.

What is also new here, beyond the new processes designed to increase the lability of the appropriate eye muscles involved, is the establishment of the appropriate number of eye blinks. These are critically required to get the crystalline lens to undergo minor periodic fluctuations. They reactivate feedback from the retinal receptors, the ciliary muscles 7, and their associated nerve 9 structures surrounding each eye. This ensures that the extrinsic eye muscles get the appropriate feedback signals directing them to contract or relax. Once they receive their cue, the now sufficiently flexible extrinsic muscles engage corrective states of contraction or extension until proper diffraction patterns are detectable at the rod and cone ends.

The blinking induces the small oscillations of the crystalline lens 6 as discussed above. For that reason, marginally impacting cataracts of the crystalline lens that are naturopathically or otherwise reversible must not be taken as an excuse to improperly remove any flexible or potentially still-flexible lens. This action always inappropriately impairs and probably even destroys the eye's natural feedback control system.

SECOND PREFERRED EMBODIMENT

From the centrally located starting point of the last complete horizontal angular excursion cycle given above, which has the nose generally aimed at the visual target, a vertical visual angular excursion is established, perpendicular to the just-finished horizontal angular activity. The technique is similar to that horizontal-excursion process introduced for the purpose of increasing the adjustability of those formerly (semi) locked extrinsic muscles. The eyes remain uncovered, and the nose initially works upward in approximately two-degree excursions (about four vertically adjacent moon heights). It is still necessary to blink as before, while the eyes are aiming downward at the just noticeably blurred visual target, at each stopping point. Upward excursion is restricted to about half of the angular range established for the horizontal track. Maximum upward displacement is to be reached in continued separate stages of two angular degrees for each individual angular displacement. Then, downward excursion, with the same sized displacements, and also with the individual (temporary) end-point blinkings, is carried out until the nose is downwardly aimed by about the same maximal angle established for the vertical upward displacement. The cycle is completed by returning to the central location. At least one additional, complete vertical cycle should be repeated.

Figure 5:
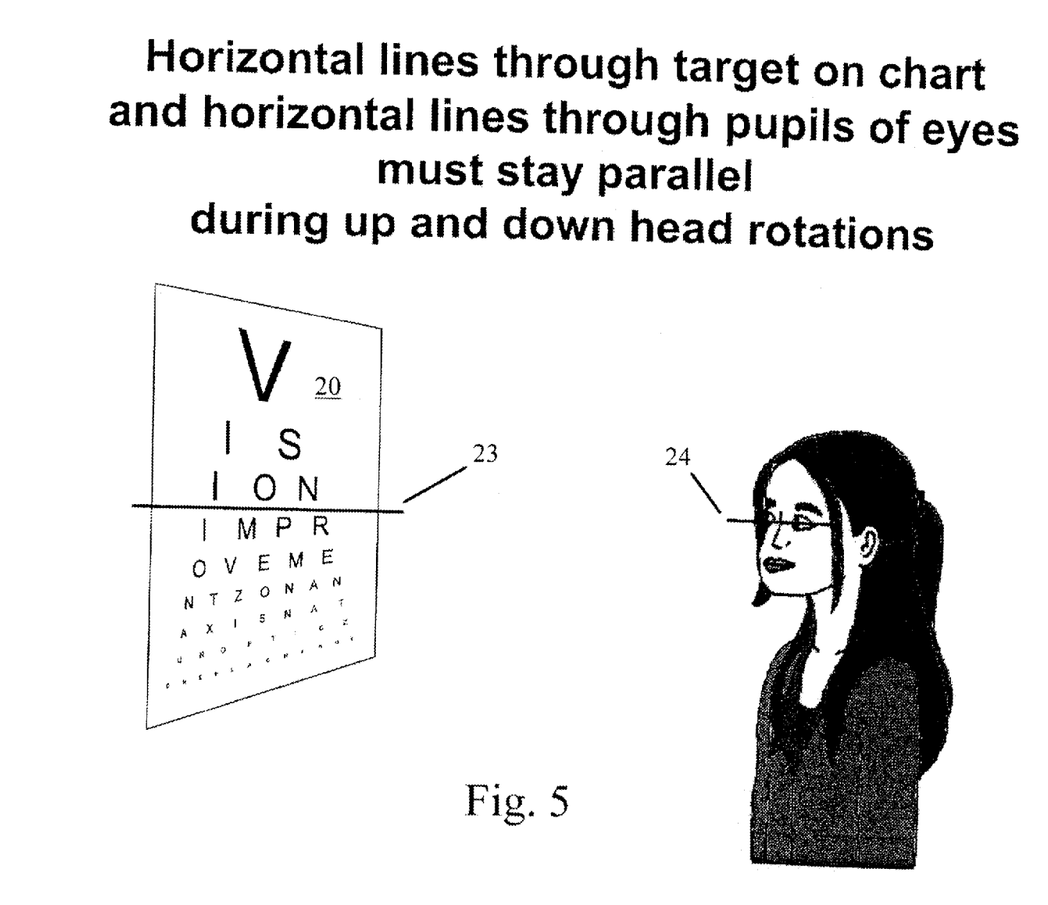
FIG. 5 depicts a subject focusing on a target chart while maintaining horizontal stability during vertical head rotation.

Referring next to FIG. 5, the subject refrains from twisting her head during the above procedure by maintaining an imaginary horizontal line 24 passing through the subject's eyes, parallel with an imaginary horizontal line 23 passing through the center of the target, 20.

Figure 6:
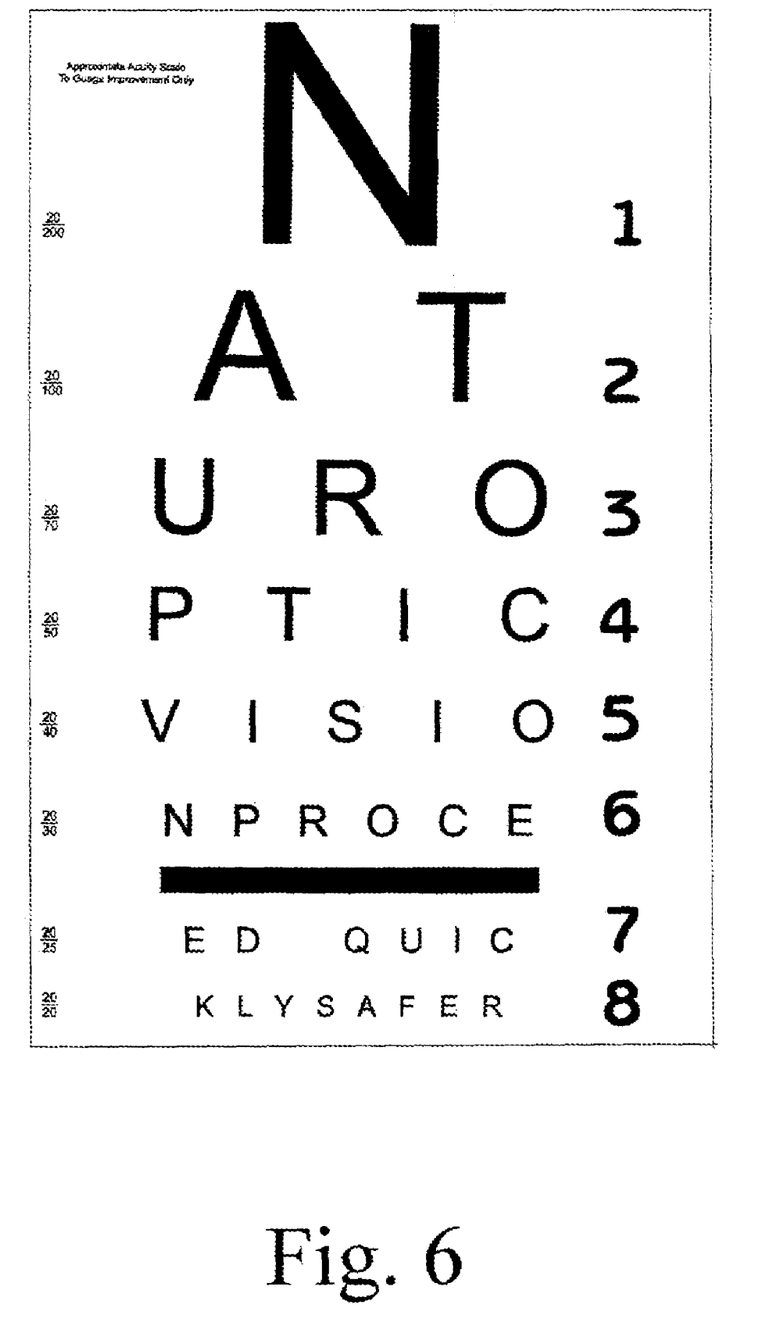
FIG. 6 depicts a typical target used in the procedures of the current invention.

Referring to FIG. 6, a typical target, used in the above procedures, is shown.

ADDITIONAL EMBODIMENTS

Other cycles are to be established, as necessary for each individual, in perpendicular orientations relative to the 'east-west' or ('north-south') horizontal (or vertical) axis previously established. These trajectories are to be monitored to ensure constant and maintained horizontal alignment of the eyes. Box-like circuits of all edge lengths are particularly effective, with 'clockwise' movement interspersed with 'counterclockwise' cycles, as appropriate.

Visual Target Alternatives

Television provides a variety of visual target possibilities. Television displays with sub-captioning, Closed Captioning or news streamers, especially high-definition processes, or movie sub-titles, are particularly effective. Further, appropriate information panel background colors such as red or maroon on cable or satellite TV systems, enhance the effectiveness of these TV displays as visual targets.

Other non-perpendicular, (diagonal) angular nose trajectories, with reverse-angular displacements for eye trajectories, can only be allowed when there is assurance, by monitoring, that the eyes remain horizontal.

As long as the eyes remain horizontally aligned, circular pathway procedures and processes incorporating the steps from above, of any desired and safe radii, can be established in the clockwise and counterclockwise senses.

FINAL EMBODIMENT OF THE INVENTION

In this embodiment of the invention the user places a sufficiently opaque pair of dark gloves, worn on the hands, or their equivalent, over both eyes, positioned so that the eyes can blink freely and fully, while ensuring that no light at all can be detected by the eyes. Any equivalent process for some individuals could include dark-painted goggles such as those used for swimming underwater, or something like appropriately darkened objects like ping pong ball halves fitted to each eye so that it is in total darkness, and so each eye can blink.

This action induces a visual dark field, which ensures that eye mechanisms automatically cause varying and increasing pupil 16 diameters. This brings longer and longer wavelength values into coincidence with cone and rod ends. The induced dark field of view for each blinking eye is now to be utilized in the following procedure to be achieved in gradual stages as appropriate.

This new embodiment requires that the fully engaged eyes be kept in their induced dark field of view, so that the blinking mechanism is activated as required at each (temporary) stopping point during the eyes' displacements. The entire vertical and horizontal angular displacement procedure outlined fully above is now to be enacted with some distant, centrally located audible signal, or its equivalent, to be used as the monitored aiming cue. Thus, the eyes of the user will attempt to focus at the location of the audible signal. This audible signal establishes a "virtual" visual target for the subject to focus on. Some appropriate substitute can be used for those who have impaired hearing.

Neither the nose nor either eyelid will be perceived at large enough angular displacements horizontally or vertically, because of the totally dark field of view which has been deliberately induced. Now, much larger angular displacements may be allowed for those individuals who have gradually and safely extended the range of flexibility of the extrinsic muscles involved. These include the superior-inferior rectus muscle pair during vertical traces, and combinations of the obliques with recti muscles on slantwise, rectangular or box-like, and circular trajectories or elliptical pathways.

The subjects should be carefully monitored while practicing this embodiment of the invention so that they continue to align their heads so that the (imaginary) parallel lines as described above remain parallel. Improper alignments may perpetuate, or worsen, systemic astigmatisms, defined below, that had been previously induced within damaged visual systems.

The new dark-field-of-view processes outlined above, with repeated cycles, and alternated with safely augmented equivalent light-field-of-view processes, will bring a previously slightly blurred state into quite rapid, clear focus. The individual can then move closer to the target to achieve a new slightly blurred visual state when the goal is to improve near vision. The procedure is repeated for both light and dark fields, as necessary, until a desired state of visual proficiency is reached. Because the blinking is also enacted during total dark field stimulus, pupil 16 diameter, a, has certainly increased, and therefore wavelength, and focal length, must increase proportionately, as required and shown and described above. In other words, the system must adjust dynamically toward longer wavelength values than had been previously in use. Change can occur because recovered muscular flexibility allows it.

Some visual systems are essentially locked into place somewhere in the long wavelength range. The combination of these dark and then light-field-of-view processes will also develop dynamic movement toward greater capability for using short wavelengths of light, when that is appropriate, again substantiated as described above.

When there is a need to improve distance vision, the required incremental cycles of yogic-like improved flexibility of the extrinsics are achieved by the actions, and for the reasons, described above.

Once dark-field limbering-up cycles are completed, they can be followed by additional light-field-of-view sequences. This repetition is only to be used for those individuals capable of continuing without some rest interval, since the process must never be allowed to recreate damaging, maintained muscle stresses equivalent to those creating the original dysfunction. When necessary, rest intervals must be encouraged. Then, close-field activities can be interspersed with alternating activities associated with distance improvement techniques.

These are always accompanied with the necessary blinking, and they will jointly bring the somewhat distant, previously slightly blurred, visual target into detectably clearer focus.

A slightly longer distance to the visual stimulus is then established, that just noticeably blurs it. Then, all prior cycles are repeated. Any desired state can be achieved with this process, with certain individuals reaching average, or 20/20, vision, or even superior visual acuity, as measurable on any calibrated chart.

Individuals with severely impaired vision may need to weaken their extreme prescription lenses or contacts gradually, instead of working directly toward non-use of artificially sustained vision, it their situation requires it. Unless these individuals pursue the corrective process diligently, they may soon revert to at least their worst prior visual acuity by sustained use of even these weaker visual aids. Glasses and contact lenses encourage the dynamically impaired system to be come more static.

So-called nearsightedness never represents correct near vision, nor does farsightedness represent proper far vision;

they only designate acceptable, but vision compromised by an actual statically fixed state. Glasses, contacts or corneal surgery of any type that is claimed to "correct" vision merely give the option of shifting one visual state for another still actually deficient static state. Information from the prior paragraphs and claims can be used to improve and/or correct these states and simultaneously improve and/or correct nearsightedness, farsightedness, astigmatism and possibly other visual defects. All that is required is reengagement of proper feedback signals that can follow reestablishing flexible extrinsic muscles, given appropriate dark-field-of-view, and corresponding light-field-of-view visual experiences, concomitant with proper horizontal and vertical head and eye displacements, and their combinations. This is explicitly different from all other vision change options. As a Naturoptic process, it can do no harm, and will provide only benefit.

While certain embodiments and examples have been used to describe the present invention, many variations are possible and are within the spirit and scope of the invention. Such variations will be apparent to those skilled in the art upon inspection of the specification and claims herein. Other embodiments are within the following claims.

What is claimed is:

1. A method for restoring healthy vision to the damaged eyes of a subject, comprising:
   (a) establishing a visual target;
   (b) during the entire time of the method,
   (1) keeping a vertical line through said visual target parallel to corresponding vertical lines through the centers of the planes of the pupils 16 of the eyes, for horizontal angular head displacements;
   (2) maintaining a line horizontally through the pupils' centers parallel to a horizontal line through the visual target, during vertical angular displacements of the head;
   (3) maintaining the fixation of the eyes on the central part of the visual target;
   (c) starting from a value of j=0, and where the starting horizontal and vertical angular displacements of the head are (0,0):
   (i) while incrementing the index i by 1, slowly rotating the subject's head by a first angle approximately $\alpha(j)\beta(j)$, where $\alpha$ is the ith horizontal excursion and $\beta(j)$ is the jth vertical excursion;
   (ii) stopping said rotating and performing about n eye blinks; and
   (iii) repeating steps (i) and (ii) of said procedure, until the total of $\tau$ steps are taken.

2. The method of claim 1, wherein
   (a) the vertical displacements $\beta(j)$ are equal to zero for all values of j, so that the head rotates only in the horizontal direction;
   (b) after j1 steps the head is at a maximum excursion $\tau 1$ to one side;
   (c) after j2 steps more, the head is at a maximum excursion $-\tau 1$ to the other side; and
   (d) after j3 steps more, the head returns to a position of (0,0).

3. The method of claim 1, wherein
   (a) the horizontal displacements $\alpha(j)$ are equal to zero for all values of j, so that the head rotates only in the vertical direction;
   (b) after j1 steps the head is at a maximum vertical excursion $\tau 2$;
   (c) after j2 steps more, the head is at a minimum excursion $-\tau 2$; and
   (d) after j3 steps more, the head returns to a position of (0,0).

4. The method of claim 1, wherein
   (a) the vertical displacements $\beta(j)$ are equal to zero for the first k values of j, so that the head rotates only in the horizontal direction for these values;
   (b) the horizontal displacements $\alpha(j)$ are equal to zero for the next l values of j, so that the head rotates only in the vertical direction for these values;
   (c) the vertical displacements $\beta(j)$ are equal to zero for the next 2k values of j, so that the head rotates only in the horizontal direction for these values, and in the direction opposite that of step (a) above, and having a total excursion equal to twice the magnitude and opposite in direction to step (a);
   (d) the horizontal displacements $\alpha(j)$ are equal to zero for the next l values of j, so that the head rotates only in the vertical direction for these values, and in the opposite direction of step (b) above and having a total excursion equal in magnitude and opposite in direction to step (b),
   so that the subject's head describes a "box" pattern, returning to the point of origin at the conclusion of the steps.

5. The method of claim 1 or 2 or 3 or 4, wherein the number of eye blinks is approximately four.

6. The method of claim 5, wherein the visual target comprises a field of high-contrast combination of thin letters, numbers or symbol sequences on a rigid background.

7. The method of claim 6, wherein each horizontal rotation of the subject's head $\alpha(j)$ has an approximate magnitude of 5 degrees for all values of j.

8. The method of claim 6, wherein each vertical rotation of the subject's head $\beta(j)$ has an approximate magnitude of 2 degrees for all values of j.

9. The method of claim 5, wherein the visual target is created by the steps of:
   (a) placing a substantially opaque cover over both eyes, positioned so that the eyes can blink freely and fully, while ensuring that no light at all can be detected by the eyes; and
   (b) sounding a distant, centrally located audible signal as an aiming cue.

10. The method of claim 9, wherein each horizontal rotation of the subject's head $\alpha(j)$ has an approximate magnitude of 5 degrees for all values of j.

11. The method of claim 9, wherein each vertical rotation of the subject's head $\beta(j)$ has an approximate magnitude of 2 degrees for all values of j.

* * * * *